United States Patent
Shaw et al.

(10) Patent No.: US 8,814,418 B2
(45) Date of Patent: Aug. 26, 2014

(54) DETACHABLE LED MODULE

(75) Inventors: Cheng-Da Shaw, Taipei (TW); Ya-Hui Chiang, Taoyuan County (TW); Hung-Lieh Hu, Hsinchu (TW); Hsin-Yun Tsai, Hsinchu County (TW); Chun-Hsing Lee, Hsinchu (TW); Chao-Wei Li, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 165 days.

(21) Appl. No.: 13/565,692

(22) Filed: Aug. 2, 2012

(65) Prior Publication Data

US 2013/0176748 A1    Jul. 11, 2013

(30) Foreign Application Priority Data

Jan. 10, 2012   (TW) .............................. 101100900 A (51) Int. Cl.
| | |
|---|---|
| *F21V 23/06* | (2006.01) |
| *G02B 6/42* | (2006.01) |
| *F21V 19/00* | (2006.01) |
| *A61B 1/06* | (2006.01) |

(52) U.S. Cl.
CPC .............. *F21V 23/06* (2013.01); *G02B 6/4261* (2013.01); *F21V 19/003* (2013.01); *A61B 1/0661* (2013.01)
USPC ............ 362/652; 362/574; 362/655; 362/555

(58) Field of Classification Search
CPC ... F21V 23/06; F21V 19/0025; F21V 19/004; F21V 19/0045; A61B 1/06; A61B 1/0661; A61B 1/0669; A61B 1/0684; A61B 1/07; G02B 6/426; G02B 6/4261; G02B 6/4275; G02B 6/4236; G02B 6/4244; G02B 6/4245; G02B 6/42; G02B 6/423; G02B 6/4201; G02B 6/4219; G02B 6/4228
USPC .......... 362/574, 312–316, 555, 652, 655–659
See application file for complete search history.

(56) References Cited

U.S. PATENT DOCUMENTS

| | | | |
|---|---|---|---|
| 5,928,133 A | 7/1999 | Halyak | |
| 6,236,622 B1 | 5/2001 | Blackman | |
| 6,588,947 B2 * | 7/2003 | Mine et al. ...................... | 385/92 |
| 6,592,269 B1 | 7/2003 | Brophy et al. | |
| 6,902,296 B2 | 6/2005 | Searfoss, III | |
| 6,998,650 B1 | 2/2006 | Wu | |
| 7,850,632 B2 | 12/2010 | Gilmour | |
| 2011/0054263 A1 | 3/2011 | Chou et al. | |
| 2011/0085758 A1 * | 4/2011 | Hodono ......................... | 385/12 |
| 2013/0051033 A1 * | 2/2013 | Kotera et al. ................. | 362/368 |
| 2013/0163261 A1 * | 6/2013 | Shimoji et al. ................ | 362/382 |

* cited by examiner

*Primary Examiner* — Diane Lee
*Assistant Examiner* — Kenny C Sokolowski (57) ABSTRACT

A modularized illuminating device includes a retaining base, a lighting module, and a light guide element. The retaining base includes an elastic positioning unit. The lighting module is removably disposed on the retaining base, and has a sliding groove and a retaining groove. The light guide element is disposed on the retaining base and faces to the lighting module. When the lighting module is installed to the retaining base along a plugging direction, the elastic positioning unit slides from the sliding groove to the retaining groove to retain the lighting module in the retaining base.

13 Claims, 8 Drawing Sheets

FIG. 8

DETACHABLE LED MODULE

CROSS-REFERENCE TO RELATED APPLICATIONS

The present application is based on, and claims priority from, Taiwan Application Serial Number 101100900, filed on Jan. 10, 2012, the disclosure of which is hereby incorporated by reference herein in its entirety.

TECHNICAL FIELD

The technical field relates to illuminating devices, and in particular to modularized illuminating devices.

BACKGROUND

In general, illuminating devices in the medical field, such as for an endoscope, utilize light emitting diode modules as light sources and emit light beams to objects via optical fibers. However, the illuminating devices have high illumination, and thus the light emitting diode module is disposed on a huge heat-dissipating device to dissipate the heat generated thereof.

Further, to force the optical fiber to align with the light emitting diode module, the light emitting diode module is locked on a retaining base with the optical fiber and the heat-dissipating device.

However, if the light emitting diode module is damaged during operation, a lot of time is spent to replace the light emitting diode module from the illuminating device. Moreover, if a medical staff does not have skilled technicians, a damaged light emitting diode module may not be repaired immediately, which may be detrimental to patients.

SUMMARY

A modularized illuminating device includes a retaining base, a lighting module, a light guide element, and a heat-dissipating element. The retaining base includes an elastic positioning unit. The lighting module is detachably disposed on the retaining base. The lighting module includes a body and a light emitting element. The body has a mounting surface facing the elastic positioning unit, a retaining groove, and a sliding groove. The retaining groove and the sliding groove are disposed on mounting surface, and communicated with each other. The light emitting element is disposed on the body. The light guide element is disposed on the retaining base, and faces the light emitting element. The heat-dissipating element is disposed on the retaining base. When the lighting module is installed on the retaining base along an inserting direction, the elastic positioning unit slides from the sliding groove to the retaining groove to force the lighting module to be retained on the retaining base.

In conclusion, the lighting module is easily installed on or removed from the retaining base by plugging. Further, by the retaining groove and the sliding groove of the lighting module and the elastic positioning unit, the lighting module is accurately aligned with the light guide element.

BRIEF DESCRIPTION OF THE DRAWINGS

The present application can be more fully understood by reading the subsequent detailed description and examples with references made to the accompanying drawings, wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 1:
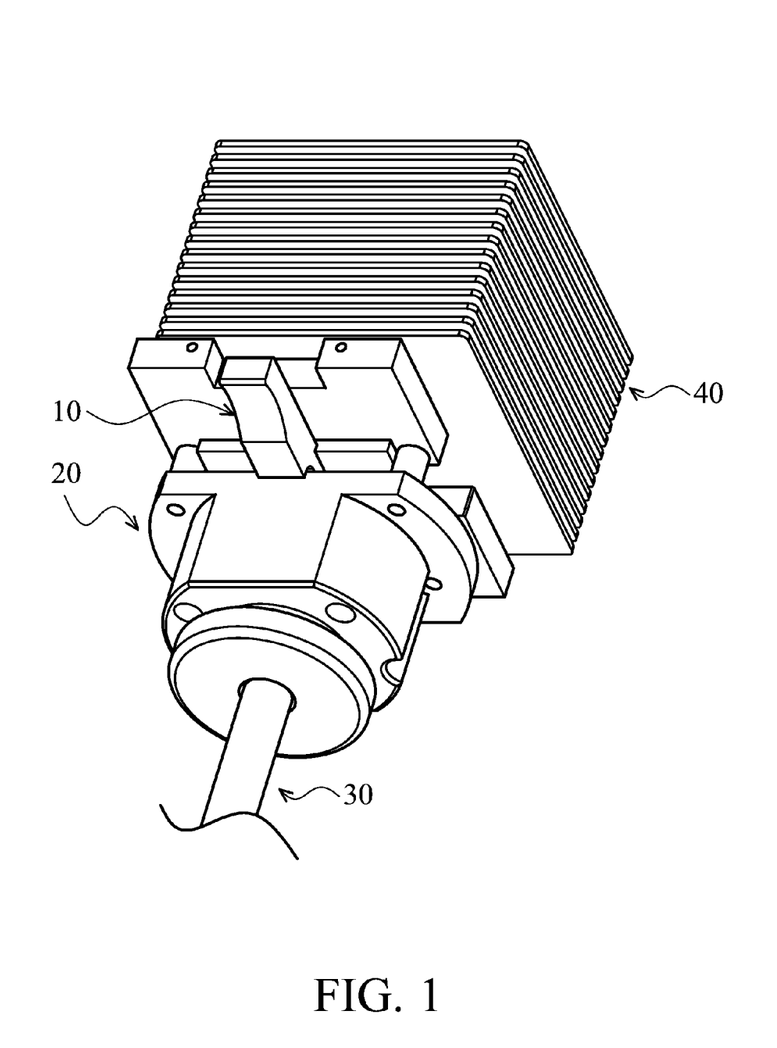
FIG. 1 is a perspective view of a modularized illuminating device in accordance with a first embodiment.

FIG. 1 is a perspective view of a modularized illuminating device 1 in accordance with a first embodiment. As shown in FIG. 1, the modularized illuminating device 1 is for illumination applied in the medical field. For example, the modularized illuminating device 1 may be applied for endoscopes. The modularized illuminating device 1 includes a lighting module 10, a retaining base 20, a light guide element 30, and a heat-dissipating element 40. The lighting module 10 is detachably disposed on the retaining base 20. The light guide element 30 may be an optical fiber disposed on the retaining base 20 corresponding to the lighting module 10. The lighting module 10 emits a light beam to an object via the light guide element 30. The heat-dissipating element 40 is disposed on the retaining base 20 to dissipate the heat generated by the lighting module 10.

Figure 2:
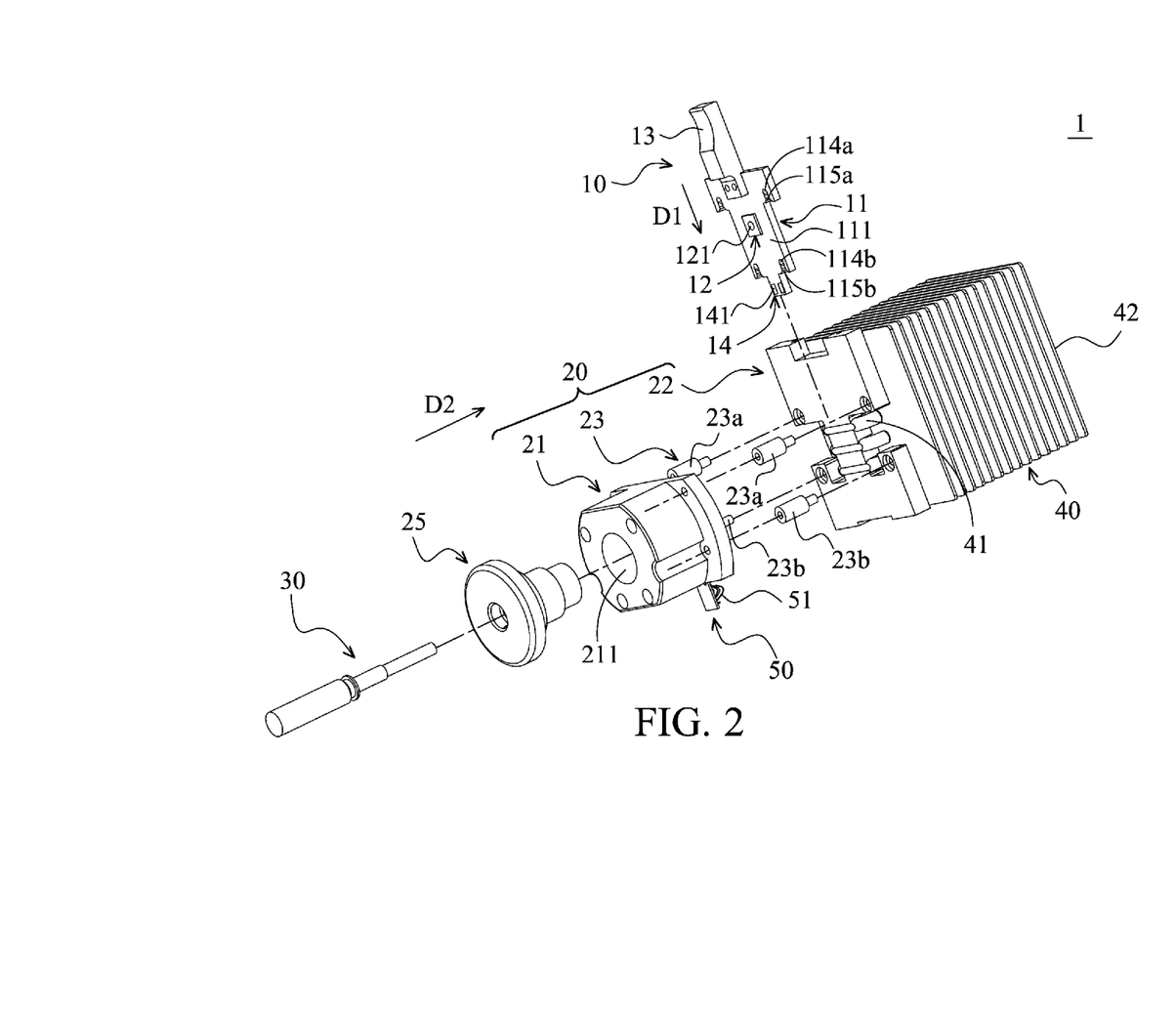
FIGS. 2 and 3 are exploded views of the modularized illuminating device in accordance with the first embodiment.
Figure 3:
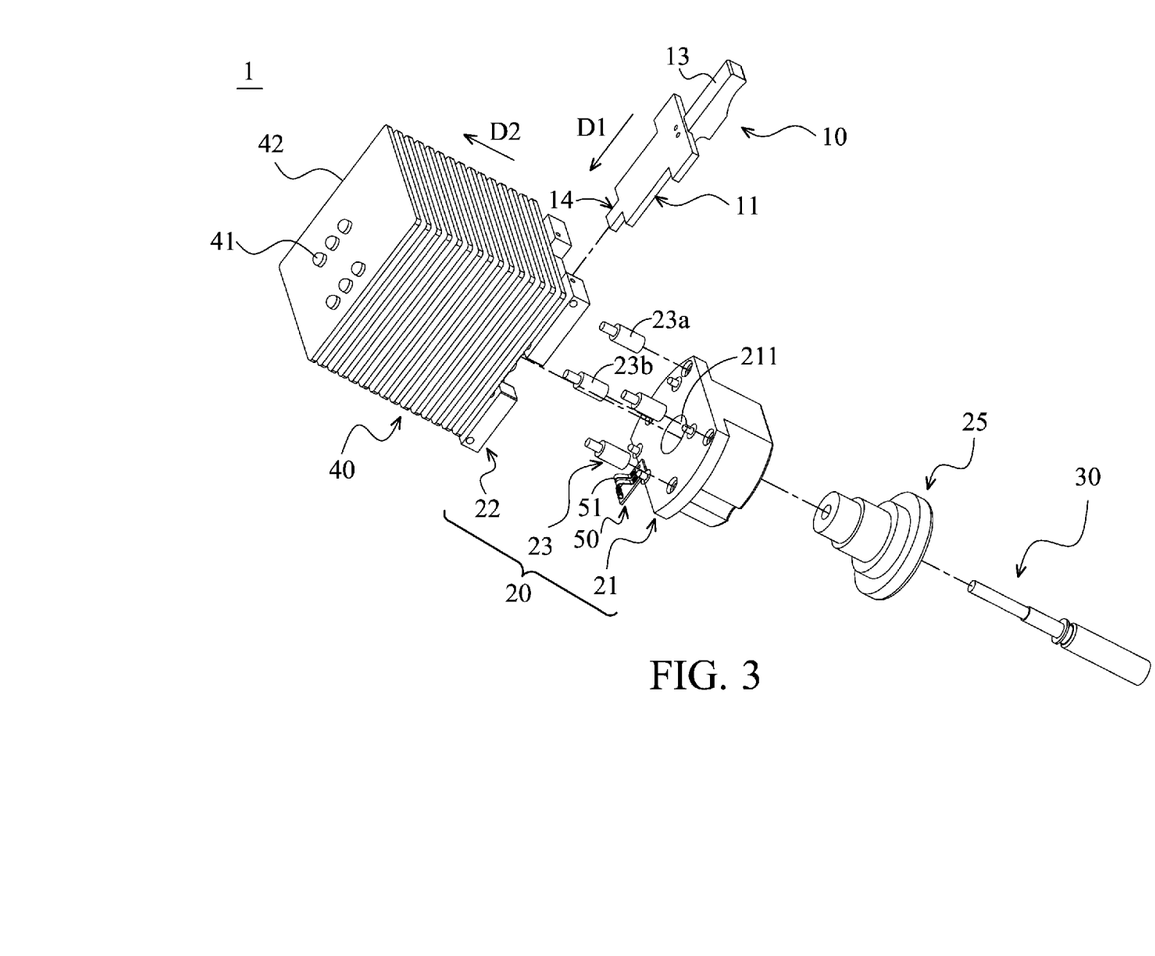
Figure 4:
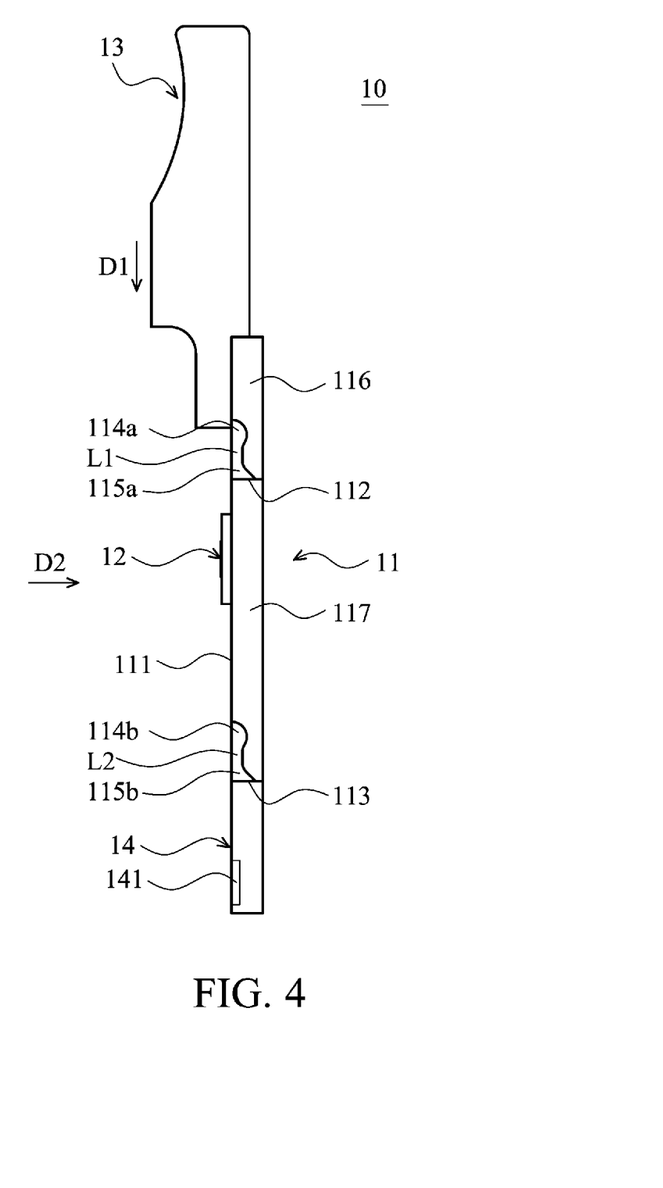
FIG. 4 is a schematic view of a lighting module in accordance with the first embodiment.

FIGS. 2 and 3 are exploded views of the modularized illuminating device 1 in accordance with the first embodiment, and FIG. 4 is a schematic view of the lighting module 10 in accordance with the first embodiment. As shown in FIGS. 2 to 4, the lighting module 10 includes a body 11, a light emitting element 12, a handle 13 and an electrode unit 14.

The body 11 is a plate structure with a T-shape. The body 11 has a mounting surface 111, a first inserting surface 112, a second inserting surface 113, a plurality of retaining grooves 114a and 114b, and a plurality of sliding grooves 115a and 115b, wherein the structures of the retaining grooves 114a and 114b may be the same, and the structures of the sliding grooves 115a and 115b may be the same. The mounting surface 111 is connected to the first inserting surface 112 and the second inserting surface 113. The mounting surface 111 is extended along an inserting direction D1, and the first inserting surface 112 and the second inserting surface 113 are extended along an extension direction D2, wherein the inserting direction D1 may be perpendicular to the extension direction D2. The retaining grooves 114a and 114b are disposed on the mounting surface 111. The bottoms of the retaining grooves 114a and 114b are arc surfaces. The sliding groove 115a is disposed on the mounting surface 111 and the first inserting surface 112, and the sliding groove 115b is disposed on the mounting surface 111 and the second inserting surface 113. The retaining groove 114a and the sliding groove 115a are communicated with each other, and the retaining groove 114b and the sliding groove 115b are communicated with each other.

As shown in FIG. 4, the depth of the sliding groove 115*a* (or 115*b*) gradually decreases from an end, which is distant from the retaining groove 114*a* (or 114*b*), of the sliding groove 115*a* (or 115*b*) to an opposite end, which is connected to the retaining groove 114*a* (or 114*b*), of the sliding groove 115*a* (or 115*b*). The bottom of the retaining groove 114*a* (or 114*b*) is deeper than a connection location L1 (or L2) between the sliding groove 115*a* (or 115*b*) and the retaining groove 114*a* (or 114*b*).

The body 11 defines a first body portion 116 and a second body portion 117 along the inserting direction D1 in sequence. The thicknesses of the first body portion 116 and the second body portion 117 are the same. The width of the first body portion 116 is wider than the second body portion 117. The second body portion 117 is extended from the central of the first inserting surface 112 of the first body portion 116. The retaining groove 114*a* and the sliding groove 115*a* are located on the first body portion 116, and the retaining groove 114*b* and the sliding groove 115*b* are located on the second body portion 117.

The light emitting element 12 is disposed on the mounting surface 111 of the second body portion 117. The light emitting element 12 may include a plurality of light emitting diodes 121 to increase the illumination thereof. The handle 13 is disposed on the first body portion 116 of the body 11, and may be held by a user.

The electrode unit 14 is perpendicularly extended from the central of the second inserting surface 113 of the second body portion 117, and coupled to the light emitting element 12. The electrode unit 14 includes a plurality of metal strips 141 coupled to the light emitting element 12.

Figure 5:
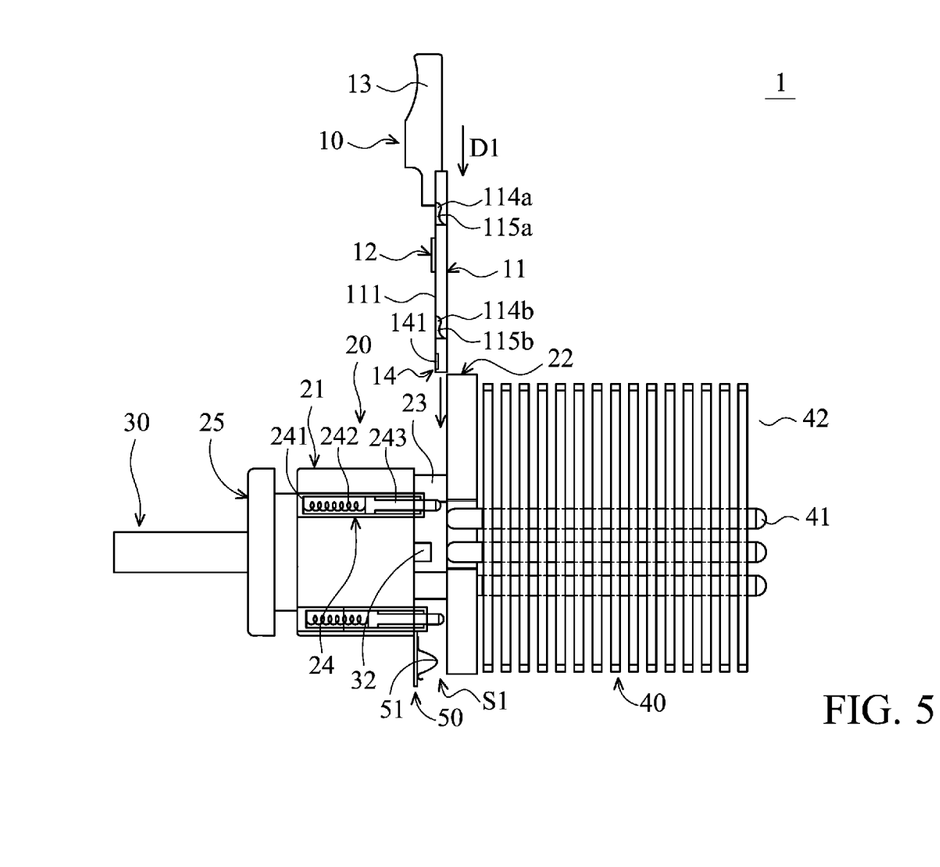
FIGS. 5 and 6 are schematic views of the modularized illuminating device in accordance with the first embodiment.

FIG. 5 is a schematic view of a modularized illuminating device 1 in accordance with the first embodiment, wherein the lighting module 10 is not inserted into the retaining base 20. As shown in FIGS. 2, 3 and 5, the retaining base 20 includes a first retaining body 21, a second retaining body 22, a plurality of spacing units 23, a plurality of elastic positioning units 24 and an optical fiber connector 25. The first retaining body 21 includes a through hole 211. The light guide element 30 penetrates through the optical fiber connector 25, and a portion of the optical fiber connector 25 is disposed on the through hole 211. When the lighting module 10 is not disposed on the retaining base 20, the light guide element 30 faces the second retaining body 22, and when the lighting module 10 is disposed on the retaining base 20, the light guide element 30 faces the light emitting element 12.

The spacing units 23 are located between the first retaining body 21 and the second retaining body 22 to form an inserting groove S1 between the first retaining body 21 and the second retaining body 22. The lighting module 10 is detachably disposed in the inserting groove S1. The distance between the two adjacent spacing units 23*a* (as shown in FIGS. 2 and 3) is substantially equal or wider than the width of the first body portion 116. The distance between the two adjacent spacing units 23*b* (as shown in FIGS. 2 and 3) is substantially equal or wider than the width of the second body portion 117. The lighting module 10 is located between the two adjacent spacing units 23*a* and the two adjacent spacing units 23*b* to retain the position of the lighting module 10.

The elastic positioning unit 24 faces the mounting surface 111 of the body 11. The elastic positioning unit 24 includes a positioning sleeve 241, a positioning spring 242 and a positioning element 243. The positioning sleeve 241 is disposed in the first retaining body 21, and the positioning spring 242 is disposed in the positioning sleeve 241. The positioning spring 242 provides an elastic force to the positioning element 243. An end of the positioning element 243 protrudes over the positioning sleeve 241, and the end of the positioning element 243 has an arc surface corresponding to the bottom of the retaining groove 114*a* (or 114*b*). Another end of the positioning element 243 is connected to the positioning spring 242.

The optical fiber connector 25 is disposed on the first retaining body 21. The light guide element 30 penetrates through the optical fiber connector 25 and the first retaining body 21 to the light emitting element 12. The light emitting element 12 emits a light beam to an end of the light guide element 30, and the light beam is emitted from another end of the light guide element 30. An endoscope (not shown in figures) may be disposed on the end of the light guide element 30.

The heat-dissipating element 40 includes a plurality of heat pipes 41 and a plurality of cooling fins 42. The heat pipes 41 are disposed on the second retaining body 22, and the cooling fins 42 are parallelly disposed on the heat pipe 41. The second retaining body 22 is made from heat conductive material. The heat generated by the light emitting element 12 is transmitted to the heat pipe 41 via the body 11 and the second retaining body 22, and the heat is dissipated from the cooling fins 42.

A power electrode unit 50 is disposed on the first retaining body 21 of the retaining base 20. In the embodiment, the power electrode unit 50 includes a plurality of elastic strips 51.

Figure 6:
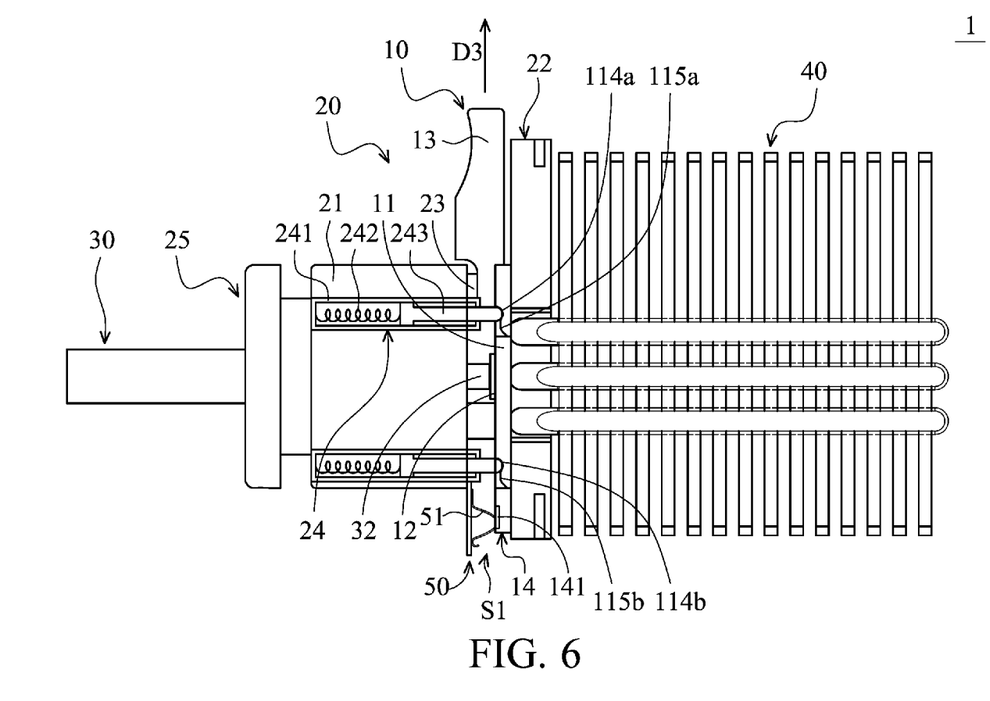

As shown in FIGS. 5 and 6, when the lighting module 10 is inserted into the retaining base 20 along the inserting direction D1, the elastic positioning unit 24 contacts the sliding groove 115*a* (or 115*b*) by passing through the inserting surface 112 (or 113). Since the depth of the sliding groove 115*a* (or 115*b*) gradually decreases from an end of the sliding groove 115*a* (or 115*b*) distant from the retaining groove 114*a* (or 114*b*) to an opposite end of the sliding groove 115*a* (or 115*b*) connected to the retaining groove 114*a* (or 114*b*), the positioning spring 242 applies an elastic force to the positioning element 243. Thus, the elastic positioning unit 24 may slide the sliding groove 115*a* (or 115*b*) to the retaining groove 114*a* (or 114*b*) when the lighting module 10 is installed on the retaining base 20 along an inserting direction D1.

Further, since the bottom of the retaining groove 114*a* (or 114*b*) is deeper than the connection location L1 (or L2) of the sliding groove 115*a* (or 115*b*) and the retaining groove 114*a* (or 114*b*), the elastic positioning unit 24 is retained in the retaining groove 114*a* (or 114*b*) by the elastic force, and the lighting module 10 is stably retained on retaining base 20.

In addition, when the elastic positioning unit 24 contacts with the retaining groove 114*a* (or 114*b*), the metal strips 141 are accurately connected to the elastic strips 51 to force the power electrode unit 50 to connect with the electrode unit 14 due to the structures of the elastic positioning unit 24 and the retaining groove 114*a* (or 114*b*).

The lighting module 10 may be removed from the retaining base 20 along a detachment direction D3 opposite to the inserting direction D1. Since the positioning element 243 is movably disposed in the positioning sleeve 241, and the top of the elastic positioning unit 24 and the bottom of the retaining groove 114*a* (or 114*b*) are arc surfaces, the user may pull the lighting module 10 from the retaining base 20 along the detachment direction D3 to replace the lighting module 10 easily.

Figure 7:
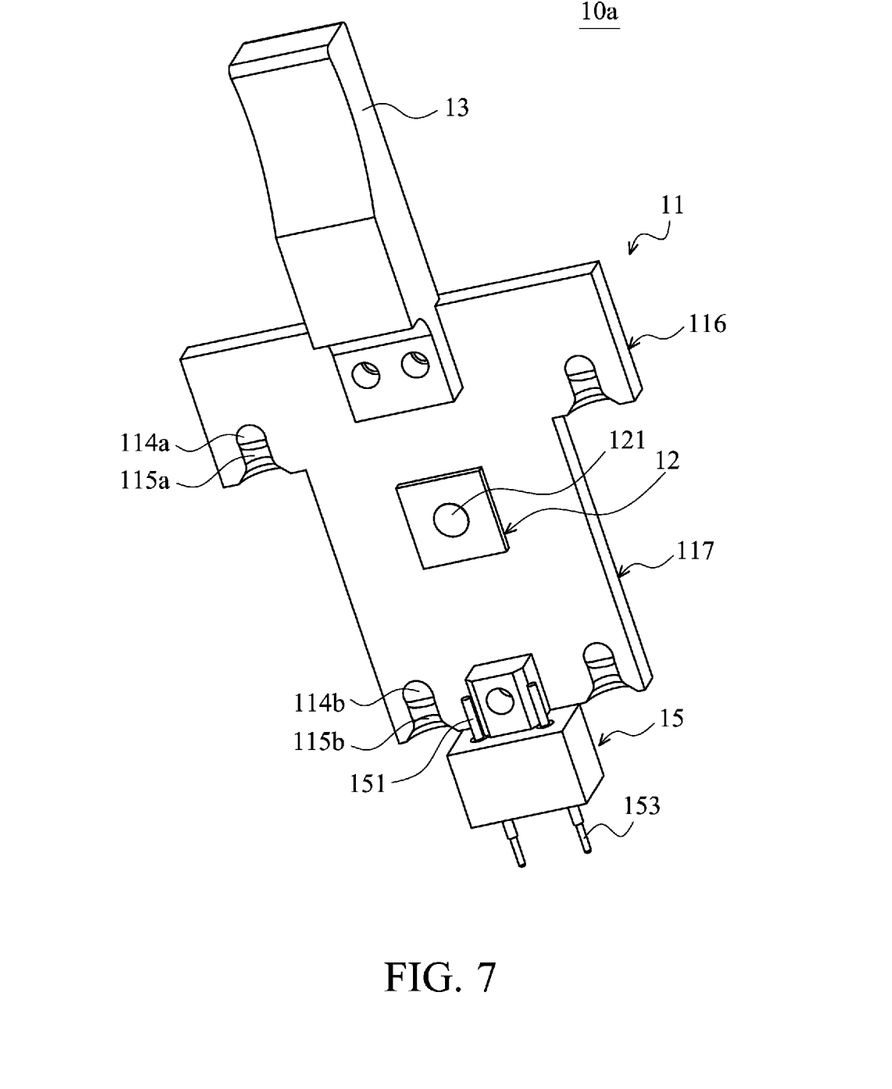
FIG. 7 is a perspective view of a lighting module in accordance with a second embodiment.
Figure 8:
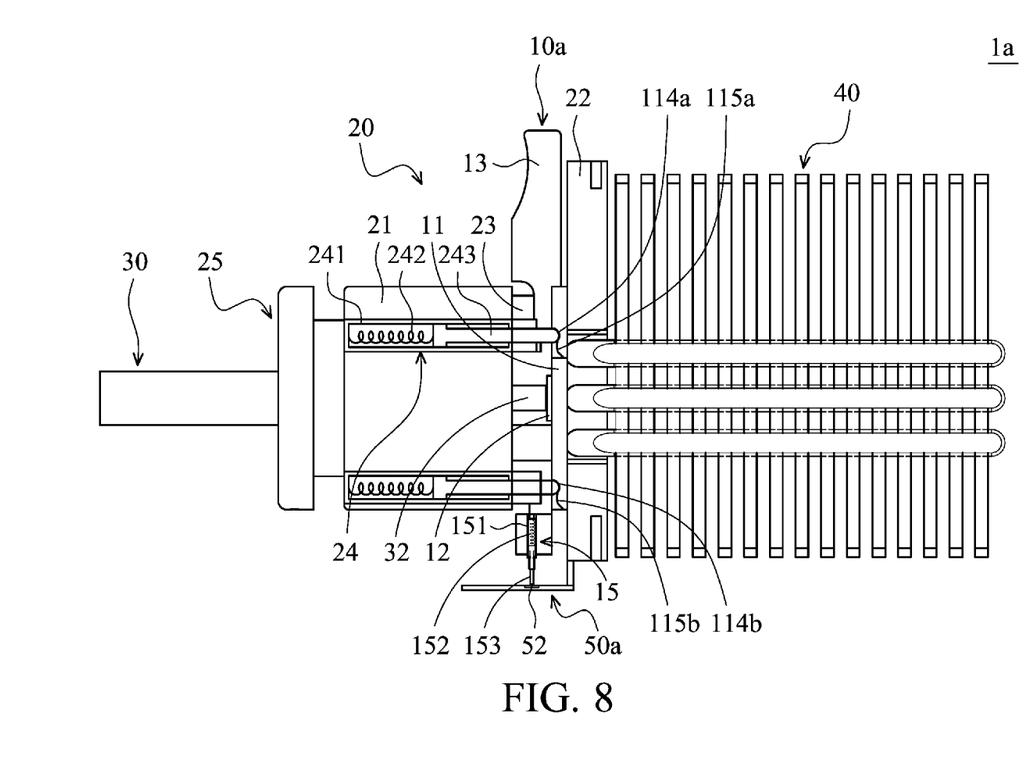
FIG. 8 is a schematic view of a modularized illuminating device in accordance with the second embodiment.

FIG. 7 is a perspective view of a lighting module 10*a* in accordance with a second embodiment, and FIG. 8 is a schematic view of a modularized illuminating device 1*a* in accordance with the second embodiment. The differences between the first embodiment and the second embodiment are described as follows. As shown in FIGS. 7 and 8, an electrode unit 15 of the lighting module 10*a* includes a terminal sleeve 151, a spring 152, and a conductive terminal 153. The spring 152 is disposed in the terminal sleeve 151. An end of the conductive terminal 153 is connected to the spring 152, and another end of the conductive terminal 153 protrudes over the terminal sleeve 151.

The power electrode unit 50a is disposed on the second retaining body 22. The power electrode unit 50a includes a metal strip 52. When the elastic positioning unit 24 contacts the retaining groove 114a (or 114b), the conductive terminal 153 contacts the metal strip 52 of the power electrode unit 50. Since the spring 152 provides an elastic force to the conductive terminal 153, the conductive terminal 153 contacts the metal strip 52, accurately.

In conclusion, the lighting module is easily installed on or removed from the retaining base by plugging. Further, by the retaining groove and the sliding groove of the lighting module and the elastic positioning unit, the lighting module is accurately aligned with the light guide element.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A modularized illuminating device, comprising:
   a retaining base comprising an elastic positioning unit;
   a lighting module detachably disposed on the retaining base, the lighting module comprising:
      a body having a mounting surface facing the elastic positioning unit, a retaining groove, and a sliding groove, wherein the retaining groove and the sliding groove are disposed on the mounting surface and communicated with each other; and
      a light emitting element disposed on the body; and
   a light guide element disposed on the retaining base,
   wherein the elastic positioning unit comprises:
      a positioning sleeve disposed in the retaining base;
      a positioning spring disposed in the positioning sleeve; and
      a positioning element, having a first end and a second end, wherein the first end is connected to the positioning spring, and the second end protrudes over the positioning sleeve,
      wherein the second end of the positioning element has and arc surface, and a bottom of the remaining groove corresponds to the arc surface;
   wherein when the lighting module is installed on the retaining base along an inserting direction, the elastic positioning unit slides from the sliding groove to the retaining groove to force the lighting module to be retained on the retaining base.

2. The modularized illuminating device as claimed in claim 1, wherein the body has an inserting surface connected to the mounting surface, and the sliding groove is disposed on the mounting surface and the inserting surface, and when the lighting module is inserted into the retaining base along the inserting direction, the elastic positioning unit contacts the sliding groove by passing through the inserting surface.

3. The modularized illuminating device as claimed in claim 1, wherein the sliding groove has a first end distant from the retaining groove and a second end connected to the retaining groove, and the depth of the sliding groove gradually decreases from the first end to the second end, and a bottom of the retaining groove is deeper than a connection location between the sliding groove and the retaining groove.

4. The modularized illuminating device as claimed in claim 1, wherein a top of the elastic positioning unit has an arc surface, and a bottom of the retaining groove corresponds to the arc surface.

5. The modularized illuminating device as claimed in claim 1, wherein the lighting module comprises a handle disposed on the body.

6. The modularized illuminating device as claimed in claim 1, wherein the lighting module includes an electrode unit disposed on the body and coupled to the light emitting element.

7. The modularized illuminating device as claimed in claim 6, further comprising a power electrode unit disposed on the retaining base, and when the elastic positioning unit contacts the retaining groove, the power electrode unit is connected to the electrode unit.

8. The modularized illuminating device as claimed in claim 7, wherein the electrode unit comprises a plurality of metal strips, and the power electrode unit comprises a plurality of elastic strips, and when the elastic positioning unit contacts the retaining groove, the metal strips are respectively connected to the elastic strips.

9. The modularized illuminating device as claimed in claim 7, wherein the electrode unit comprises:
   a terminal sleeve;
   a spring disposed in the terminal sleeve; and
   a conductive terminal having a first end connected to the spring, and a second end protruding over the terminal sleeve,
   wherein when the elastic positioning unit contacts the retaining groove, the conductive terminal is connected to the power electrode unit.

10. The modularized illuminating device as claimed in claim 1, wherein the retaining base comprises a first retaining body, a second retaining body and a plurality of spacing units, and the spacing units are connected to the first retaining body and the second retaining body to form an inserting groove between the first retaining body and the second retaining body, wherein the lighting module is detachably disposed in the inserting groove.

11. The modularized illuminating device as claimed in claim 10, further comprising a heat-dissipating element disposed on the second retaining body.

12. The modularized illuminating device as claimed in claim 1, wherein the retaining base comprises an optical fiber connector.

13. The modularized illuminating device as claimed in claim 12, wherein the light guide element is an optical fiber penetrating through the optical fiber connector and the retaining base to the light emitting element, wherein the light emitting element emits a light beam to an end of the optical fiber, and the light beam is emitted from another end of the optical fiber.

* * * * *